United States Patent [19]

Brazhnikov

[11] 4,117,732

[45] Oct. 3, 1978

[54] METHOD FOR CHECKING THICKNESS OF SHEET MATERIALS BY USING ACOUSTIC OSCILLATION AND DEVICE FOR EFFECTING SAME

[76] Inventor: Nikolai Ivanovich Brazhnikov, 1 ulitsa Bebelya 3, korpus 11, kv. 48, Moscow, U.S.S.R.

[21] Appl. No.: 658,478

[22] Filed: Feb. 17, 1976

[51] Int. Cl.² ............................................. G01B 17/00
[52] U.S. Cl. ...................................................... 73/599
[58] Field of Search ................... 73/67.5 R, 67.6, 599; 72/16

[56] References Cited

U.S. PATENT DOCUMENTS

| | | | |
|---|---|---|---|
| 2,431,862 | 12/1947 | Carlin | 73/67.6 |
| 2,483,821 | 10/1949 | Firestone | 73/67.6 |
| 2,612,772 | 10/1952 | McConnell | 73/67.5 R |
| 3,033,029 | 5/1962 | Weighart | 73/67.8 R |
| 3,074,267 | 1/1963 | Martin | 73/67.5 R |
| 3,401,547 | 9/1968 | Hall et al. | 73/67.5 R UX |

OTHER PUBLICATIONS

B. Carlin, Ultrasonics, 1960, McGraw-Hill Book Co., pp. 200–203.

*Primary Examiner*—Richard C. Queisser
*Assistant Examiner*—John P. Beauchamp
*Attorney, Agent, or Firm*—Lackenbach, Lilling & Siegel

[57] ABSTRACT

Disclosure is made of a method for checking the thickness of sheet materials, whereby acoustic oscillation is sent in the form of a traveling wave through a material being checked roughly perpendicularly to its surface. The amplitude of the acoustic oscillations that have passed through the material being checked is measured and compared to that of a reference signal, whereby the thickness of the sheet material is determined. The proposed device for checking the thickness of sheet materials comprises an acoustical radiator and an acoustical receiver. The working surface of the radiator and receiver are roughly parallel to the surface of a material being checked, which material is placed between the radiator and receiver. The distance between the radiator and receiver is selected to be in excess of the spatial extension of the traveling wave during each measurement period. The device further comprises a measuring unit which includes in series connection the receiver, an amplifier, a peak detector, and a unit for comparing a reference signal and a signal carrying information of the thickness of the sheet material being checked. Connected to the comparison unit are a reference signal setter and a recorder. The proposed method for checking the thickness of sheet materials and device for effecting this method ensures high accuracy of measurements within a broad range of values being measured.

12 Claims, 2 Drawing Figures

METHOD FOR CHECKING THICKNESS OF SHEET MATERIALS BY USING ACOUSTIC OSCILLATION AND DEVICE FOR EFFECTING SAME

The present invention relates to the use of acoustic oscillation for automatically checking production processes and, more particularly, to a method for checking the thickness of sheet materials by using acoustic oscillation and a device for effecting this method.

The invention is applicable to automatic systems for controlling rolling mills in ferrous and non-ferrous metallurgy, as well as in machine building, polymer and pulp and paper industries for automatic contactless checking of the thickness of thin-sheet and film materials (with the sheet thickness of less than 0.5 to 1 mm).

There is known a method for measuring the thickness of thin-sheet materials.

According to this method, a sheet material being checked is exposed to penetrating radiation and the degree of the attenuation of radiation that has passed through the material is measured. The value thus obtained is indicative of the thickness of the sheet material being measured.

This method, however, is only applicable within a narrow thickness range due to the exponential dependence of the degree of attenuation upon the thickness of the material.

Besides, the method under review entails considerable errors in measuring the thickness of thin-sheet materials. This is due to the fact that the attenuation of radiation in a thin-sheet material is small and commensurable with the attenuation of radiation in the protective screen of the radiation source.

There is known a thickness gauge for effecting the foregoing method. It comprises a radioisotope radiation source and a radioisotope radiation receiver which are placed on both sides of a material being checked, as well as an electronic measuring unit connected to the receiver.

In using the thickness gauge under review, for example, for checking the thickness of rolled steel sheets, it is prohibited, for safety considerations, to place a radioisotope source next to the rolls of a rolling mill.

This results in a considerable time delay of entering information on the thickness of the sheet material being checked into the automatic mill control system, which may affect the quality of the rolled sheets.

In addition, the use of the above thickness gauge necessitates the use of protective equipment and special storerooms for storing the measuring equipment or the radioisotope radiation source during repair and adjustment periods.

Radioisotope radiation sources employed in thickness gauges of this type are expensive; their service life is short due to a limited half-life of the isotope. This necessitates periodic replacement of the radioisotope sources, which accounts for complications and high costs involved in using such thickness gauges.

There is known a method for checking the thickness of sheet materials by using acoustic oscillation.

According to this method, acoustic oscillation is periodically sent, in an acoustically conducting medium, such as flow of liquid, through a sheet material being checked. The acoustic oscillation is directed so that it is roughly perpendicular to the surface of the material. The time during which the acoustic oscillation passes through the acoustically conducting medium and the material is measured, for example, by a phase meter, and from it, the thickness of the material is determined.

However, when applied to thin-sheet materials, the foregoing method entails considerable errors in the measurements. This is due to the fact that the absolute time values of the passage of acoustic oscillation through the thin-sheet material are extremely small (in the order of $10^{-8}$ sec).

Besides, the method under review is bound to produce errors due to the formation of standing waves, which, in turn, is due to the reflection of acoustic oscillation by the surfaces of the radiator, receiver and the material being checked and the superposition of the reflected acoustic oscillation upon the oscillation that has passed through the sheet material. In order to reduce the errors, the sheet material whose thickness is being measured must be placed in the node or oscillation loop, which is done with the aid of special devices for automatically shifting the radiator and receiver relative to the material being checked. This accounts for sophisticated and costly equipment which is used to effect the method under review.

At the same time, considerable errors in thickness measurements are due to the fact that the propagation velocity of acoustic oscillation in the flow of liquid and, consequently, the propagation time depend upon the temperature of the flow. Variations in the flow temperature change the propagation velocity of acoustic oscillation, which accounts for bad errors in thickness measurements.

The reason is that for working gap widths selected to meet the production requirements (the distance between the acoustical radiator and receiver), the propagation time of acoustic oscillation in liquid is two orders greater than the recorded time of passage of oscillation through a thin-sheet or film material whose thickness is being measured. Hence, even an insignificant relative change of time of propagation of acoustic oscillation in the liquid flow, due to variations in temperature, brings about a significant absolute change in the total propagation time, commensurable with the recorded time of passage of oscillation through the thin-sheet material being checked. For example, with a foil thickness of 0.06 mm and a working gap of 60 mm, the propagation time of oscillation in liquid is 40 mcsec, whereas the recorded time or propagation of oscillation in the foil is 0.03 mcsec. A temperature change of ultrasound velocity in water, equal to 1.5 cm/sec/°C, causes a 0.04 mcsec/°C increase in the oscillation propagation time in liquid, which amounts to 130% of error per 1°.

Temperature compensation can reduce the error, yet it is impossible to attain a required accuracy because of the non-uniform distribution of temperature along the length of the liquid jet, which distribution, in addition, changes with time. As a result, the method in question is only applicable in situations when there are no significant changes in the ambient air temperature.

There is known a device for checking the thickness of sheet materials according to the foregoing method.

This device comprises an acoustical radiator and an acoustical receiver with a material being checked placed therebetween. The working surfaces of the radiator and receiver are roughly parallel to the surface of the material. An excitation voltage generator is connected to the acoustical radiator. The device also includes a measuring unit which comprises an amplifier connected to the receiver, a time measuring unit of the oscillograph or phase meter type, and a recorder. The above-mentioned subunits of the measuring unit are interconnected in series. The device further includes a time delay unit connected to the measuring unit and the excitation voltage generator.

However, the device under review cannot be used for measuring the thickness of sheet materials with considerable sagging along the length of the material. This is due to a small working gap which is the distance between the radiator and receiver. An increase in the working gap sharply raises the error in thickness measurements, because the measuring unit registers any change in the complete propagation time between the radiator and the receiver. Such time variations may be due both to a change in the thickness of the material being checked and a change in the working gap. As a result, even a negligibly small relative change in the gap width in the course of operation may lead to great measurement errors. For example, for a 60 mm gap, a 1/10,000, i.e. a 0.006 mm change in the gap's width accounts for an error of about 10% in measuring the thickness of 0.06 mm foil.

It is an object of the present invention to provide a method for checking the thickness of sheet materials by using acoustic oscillation and a device for effecting this method, which would make it possible to carry out thickness measurements within a wide range.

It is another object of the invention to raise the accuracy of measuring the thickness of sheet materials.

It is still another object of the invention to provide for accurate thickness measurements of sheet materials with considerable sagging along their length.

It is yet another object of the invention to facilitate maintenance of the device for checking the thickness of sheet materials.

The foregoing objects are attained by providing a method for checking the thickness of sheet materials by using acoustic oscillation, whereby a sheet material to be checked is placed in an acoustically conducting medium, whereupon acoustic oscillation is periodically passed through said material roughly perpendicular to the surface of said material, and parameters of the acoustic oscillation that has passed through the material being checked are measured, said method being characterized in that according to the invention, acoustic oscillation is sent through the material being checked in the form of a traveling wave, the thickness of the material being derived from the value obtained by comparing the amplitude of the traveling wave that has passed through the material being checked with the amplitude of a reference signal.

It is expedient that the acoustic oscillation frequency should be selected so that the length of the traveling wave in the sheet material being checked is greater than four maximum thicknesses of the material put together.

It is expedient that the function of the reference signal should be performed by a travelling wave that has passed through a sheet material with a predetermined thickness, the thickness of the sheet material that is being checked being determined from the difference between the amplitude of the traveling wave that has passed through the sheet material with a predetermined thickness, and the amplitude of the traveling wave that has passed through the sheet material whose thickness is being measured.

It is also expedient that the function of the reference signal should be performed by a traveling wave that has passed through a sheet material having a preselected thickness, whereas the thickness of the material being checked is determined from the ratio between the amplitude of the traveling wave that has passed through the sheet material with a preselected thickness, and that of the traveling wave that has passed through the sheet material whose thickness is being measured.

The function of the reference signal may also be performed by a traveling wave passed through a sheet material being checked, the thickness of said material being checked being found from the ratio between the amplitude of a traveling wave that is being sent through the sheet material being checked, and the amplitude of the traveling wave that has already passed through said sheet material being checked.

The objects of the present invention are also attained by providing a device for effecting the proposed method for checking the thickness of sheet material by using acoustic oscillation, comprising an acoustical radiator and an acoustical receiver, whereas a sheet material being checked is placed therebetween, the working surfaces of said radiator and receiver being roughly parallel to the surface of the sheet material being checked, and a measuring unit connected to the acoustical receiver, in which device the distance between the working surfaces of the radiator and receiver is selected, in accordance with the invention, to be in excess of the spatial extension of the traveling wave during each measurement period, the measuring unit comprising an amplifier whose input is connected to an output of the acoustical receiver, a peak detector whose input is connected to an output of the amplifier, a reference signal setter, a unit for comparing the reference signal and a signal carrying information on the thickness of the sheet material being checked, one of its inputs being connected to an output of the peak detector, its other input being connected to the reference signal setter, and a recorder connected to an output of said comparison unit.

It is expedient that the setter of the reference signal, whose function is performed by a traveling wave that has passed through a sheet material having a predetermined thickness, be constructed as an adjustable d.c. source; it is also expedient that the unit for comparing the reference signal to a signal carrying information on the thickness of the material being checked be constructed as a subtracting unit and directly connected to the adjustable d.c. source.

It is advisable that provision should be made for an additional acoustical radiator to radiate oscillation to be passed through a sheet material having a predetermined thickness; it is expedient that the setter of the reference signal, whose function is performed by a traveling wave that has passed through the sheet material with a predetermined thickness, should be constructed as an additional acoustical receiver to receive acoustic oscillation that has passed through the sheet material with a predetermined thickness, said material being arranged between said additional radiator and said additional receiver whose working surfaces are roughly parallel to the surface of said material, the distance between them being approximately equal to the distance between the working surfaces of the main radiator and main receiver; it is expedient that the unit for comparing the reference signal to a signal carrying information on the thickness of the sheet material being checked should be constructed as a division unit, said division unit being electrically connected to said additional receiver via an additional amplifier and an additional peak detector connected in series to the additional receiver.

The setter of the reference signal, whose function is performed by a traveling wave sent through the sheet material being checked, may be constructed as an additional acoustical receiver arranged between the acoustical radiator and the sheet material being checked across the path of the traveling wave so that some part of the traveling wave passes through the material being checked to the main acoustical receiver, by-passing the additional receiver, the comparison unit being constructed as a division unit, said additional receiver being electrically connected to said division unit via an additional amplifier and an additional peak detector placed in series with the additional receiver.

The proposed method for checking the thickness of sheet materials by using acoustic oscillation and the device for effecting this method have a number of advantages over the known methods and devices.

The method and device of the present invention substantially reduce errors in measuring the thickness of sheet materials and thus raise the accuracy and reliability of measurements.

In the first place, the proposed method and device completely rule out errors in thickness measurements, which are due to the formation of standing waves as a result of the reflection of acoustic oscillation from the surfaces of the radiator, receiver and material being checked and superposition of that oscillation upon the acoustic oscillation, that has passed through the material. This has been made possible because according to the proposed method, acoustic oscillation is sent through the sheet material being checked in the form of a traveling wave. In the proposed device, a traveling wave is produced due to the fact that the distance between the working surfaces of the radiator and receiver is selected to be in excess of the spatial extension of the traveling wave during each measurement period. As a result, the acoustic oscillation, reflected from the surfaces of the material being checked and the receiver, is not superposed over the acoustic oscillation that has passed through the sheet material, so that no standing waves are produced. Owing to this advantage, the proposed device needs no special means to automatically shift the acoustical radiator and receiver relative to the material being checked in order to place the latter in the node or oscillation loop of the standing wave. This factor simplifies maintenance of the proposed device for checking the thickness of sheet materials.

In the second place, the proposed method and device considerably decrease errors due to variations in the working gap width, as well as due to the fact that propagation velocity of acoustic oscillation in an acoustically conducting medium and, consequently, the time of propagation of acoustic oscillation in that medium, are dependent upon the temperature of the medium. Minimization of such errors is crucial in measuring the thickness of thin-sheet and film materials.

The latter advantage is due to the fact that according to the proposed method for checking the thickness of sheet materials, the parameter, which is indicative of the material's thickness, is the amplitude of acoustic oscillation sent through the sheet material, which is measured by the above-mentioned measuring unit of the proposed device. The acoustic oscillation amplitude is independent of variations in the working gap width, being only dependent upon the propagation velocity of acoustic oscillation in an acoustically conducting medium.

As a result, the error due to variations in the propagation velocity of acoustic oscillation in an acoustically conducting medium is reduced 5- to 10-fold. This can be illustrated by the following relation:

$$\delta d_1 = K_o \cdot (H/d_o) \cdot (\Delta C/C_o),$$

where $\delta d_1$ is an error in measuring the thickness $d_o$ of a sheet material being checked, due to a change in the velocity $C_o$ of propagation of oscillation in an acoustically conducting medium by a value of $\Delta C$, while using the known checking method;

$H$ is the width of the working gap;

$K_o$ is the constant factor.

While using the proposed method for checking the thickness of sheet materials, the error $\delta d_2$ in measuring the thickness $d_o$, due to a change by $\Delta C$ of the velocity $C_o$, is determined by the following relation:

$$\delta d_2 = K_o \cdot (\Delta C/C_o);$$

hence, $$\delta d_1/\delta d_2 = H/d_o$$

Normally, $$\delta H/\delta d_o = 5 \div 10;$$

hence, $$\delta d_1/\delta d_2 = 5 \div 10.$$

In addition, the accuracy of measuring the thickness of a sheet material being checked is raised due to the selection of an acoustic oscillation frequency at which the length of the traveling wave in the sheet material being checked is in excess of four thicknesses of said material put together.

This is due to the fact that the dependence of the amplitude of the traveling wave being passed through a sheet material upon the thickness of said material is linear only in the initial portion. As the thickness of the sheet material is increased to reach a value close to a quarter of the traveling wave length in the sheet material being checked, said dependence becomes non-linear; moreover, when the above-mentioned value is surpassed, the above-mentioned dependence is no longer single-valued. The selection of an acoustic oscillation frequency at which the maximum thickness of the sheet material being checked is not in excess of one quarter of the traveling wave length in the material being checked makes it possible to measure the amplitude while the thickness of the sheet material is changed over the linear portion of said single-valued dependence. This raises the accuracy of measurements.

The proposed method makes it possible to expand the range of measuring the thickness of sheet materials in the small-thickness area as a result of an increased sensitivity. The latter is due to the fact that the parameter, which is indicative of the thickness of a material being checked, is the amplitude of acoustic oscillation. The amplitude of acoustic oscillation that has passed through the material being checked is inversely proportional to the thickness of the material being checked and practically independent of the width of the working gap. As a result, the variation magnitude of the amplitude of acoustic oscillation passing through a thin-sheet material is normally sufficient to be measured by the above-mentioned measuring unit of the proposed device.

The proposed method for checking the thickness of sheet materials and the device for effecting this method, wherein the reference signal is a traveling wave that has passed through a sheet material possessing a predetermined thickness, whereas the reference signal setter is an adjustable d.c. source, make for a simple and sufficiently accurate checking of thicknesses of sheet materials within a thickness range of 20 to 40 percent of the predetermined thickness. In order to expand the range of measurements, the d.c. source has to be readjusted.

The fact that the function of the reference signal is performed by a traveling wave that has passed through a sheet material with a preselected thickness, and that the function of the reference signal setter is performed by an additional acoustical receiver to receive acoustic oscillation that has passed through said material, and, finally, the fact that the function of the comparison unit is performed by a division unit, all make it possible to measure thicknesses of sheet materials within a broad range without readjusting the reference signal setter.

Besides, the proposed method and device reduce errors due to the non-stability of the transmission coefficient of acoustic oscillation through a material being checked. This is due to the fact that the non-stability of said coefficient, resulting, for example, from changes in the density or temperature of the ambient air, or the atmospheric pressure, is the same for the sheet material being checked and for the sheet material with a predetermined thickness, both materials being found in immediate proximity to each other.

In addition, the foregoing embodiment of the proposed method and device makes it possible to raise the accuracy of measurements by ensuring a linear and directly proportional dependence of the output signal of the division unit upon the thickness of the material being checked. This is due to the fact that the amplitude of acoustic oscillation that has passed through the sheet material being checked is inversely proportional to the latter's thickness: hence, if it is used as a divisor, the quotient is in direct proportion to the thickness.

The fact that the function of the reference signal is performed by a traveling wave sent through a sheet material being checked, and that the function of the reference signal setter is performed by an additional receiver of said acoustic oscillation rule out measuring errors due to instability of the output power of the generator, as well as instability of the acoustical radiator. In this case, the foregoing instabilities equally affect the acoustic oscillation being passed through the sheet material being checked, and the acoustic oscillation that has already passed through said material.

The foregoing embodiment of the proposed method and device also ensures a directly proportional dependence of the output signal of the division unit upon the thickness of the sheet material being checked.

Other objects and advantages of the present invention will become more apparent from the following detailed description of preferred embodiments thereof taken in conjunction with the accompanying drawings, wherein.

Figure 1:
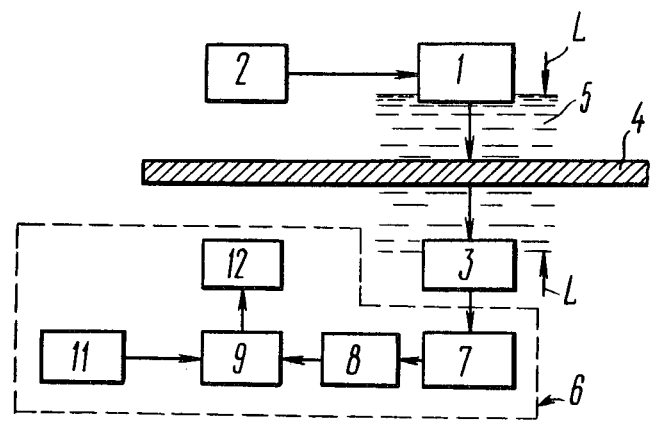
FIG. 1 is a block diagram of a device for effecting the proposed method for checking the thickness of sheet materials in accordance with the invention.

Referring now to the accompanying drawings, the device for effecting the proposed method for checking the thickness of sheet materials comprises an acoustical radiator 1 (FIG. 1), to which there is connected a generator 2, and an acoustical receiver 3. The radiator 1 is a known piezoelectric radiator (cf. U.S. Pat. No. 3,287,692). The generator 2 is built around a known shock excitation circuit (cf. U.S. Pat. No. 3,282,086). The design of the receiver 3 is also known and similar to that of the radiator 1.

Arranged between the radiator 1 and the receiver 3 is a sheet material 4 being checked. The material 4 is found in an acoustically conducting medium 5. In the case under review, the medium 5 is water warmed up to a temperature of 70° to 80° C. Water is supplied in the form of a flow whose direction is indicated by the arrow L.

The working surfaces of the radiator 1 and the receiver 3 are roughly parallel to the surface of the sheet material 4. This makes it possible to send acoustic oscillation in the acoustically conducting medium 5 through the material 4 so that the acoustic oscillation is directed roughly at a perpendicular to the surface of said material 4.

The distance between the working surfaces of the radiator 1 and the receiver 3 is selected to be in excess of the spatial extension of the traveling wave or space occupied by the travelling wave when transmitted into the conducting medium over a specified time interval within one measurement period. This makes it possible to send acoustic oscillation from the radiator 1 through the material 4 being checked in the form of a traveling wave. As a result, the formation of standing waves is ruled out; hence, there are ruled out errors in measuring the thickness of the sheet material 4, which are due to the presence of standing waves. At the same time, it becomes possible to dispense with special means to automatically shift the radiator 1 and the receiver 3 relative to the material 4 in order to place the latter in the node or oscillation loop of the traveling wave. The result is simplified maintenance of the proposed device.

Connected to the acoustical receiver 3 is a measuring unit 6. The measuring unit 6 comprises an amplifier 7 built around a known transistorized circuit. An input of said amplifier 7 is connected to an output of the receiver 3. Connected to an output of the amplifier 7 is a peak detector 8 built around a known transistor-diode circuit, its detection constant being more than one order in excess of the period of the acoustic oscillation being radiated.

It is more preferable to employ the peak detector 8 in the measuring unit 6 than amplitude or amplitude-phase detectors employed in known devices for checking the thickness of sheet materials, because said peak detector 8 makes it possible to avoid the recording of acoustic oscillations repeatedly reflected from the surfaces of the radiator 1, receiver 3 and material 4, whose amplitude is less than that of acoustic oscillations that have passed through the material 4 being checked. Connected to an output of the peak detector 8 is one of inputs of a unit for comparing a reference signal to a signal carrying information on the thickness of the material 4 being checked. In the embodiment under review, said comparison unit is constructed as a subtracting unit 9.

The subtracting unit 9 is constructed by using a known discriminator circuitry (cf. U.S. Pat. No. 3,265,151).

A signal carrying information on the thickness of the material 4 is a traveling wave that has passed through said material 4. According to the present embodiment, the reference signal is a traveling wave that has passed through a sheet material 10 (FIG. 2) with a predetermined thickness. Prior to measuring the thickness of the material 4 (FIG. 1), the material 10 is placed between the radiator 1 and the receiver 3 the way the material 4 is placed. Acoustic oscillation radiated by the radiator 1 is sent through the material 10 in the form of a traveling wave whose amplitude is then measured.

Connected to another input of the subtracting unit 9 is a reference signal setter constructed as an adjustable d.c. source 11. The output voltage of the source 11 is directly proportional to the measured amplitude of the traveling wave that has passed through the sheet material 10 with a preselected thickness. Connected to an output of the subtracting unit 9 is a recorder 12 of a known design (cf. U.S. Pat. No. 3,345,861). The scale of the recorder is graduated in thickness units.

The foregoing embodiment is the simplest. Yet this device is capable of carrying out thickness measurements only within a relatively narrow range of 20 to 40% of a preset thickness. In order to expand the range of measurements, it is necessary to change the output voltage of the d.c. source 11.

In view of this, the embodiment under review can be employed in automatic systems for controlling production processes which only require information on changes in the thickness of a sheet material being checked with respect to a predetermined value. In order to raise the reliability of the checking, it is necessary to ensure stable properties of the acoustically conducting medium 5, as well as stable radiation. This purpose can be attained through the use of a thermostated liquid, for example, water, as the acoustically conducting medium 5, as well as through the use of a high-stability radiator 1.

Figure 2:
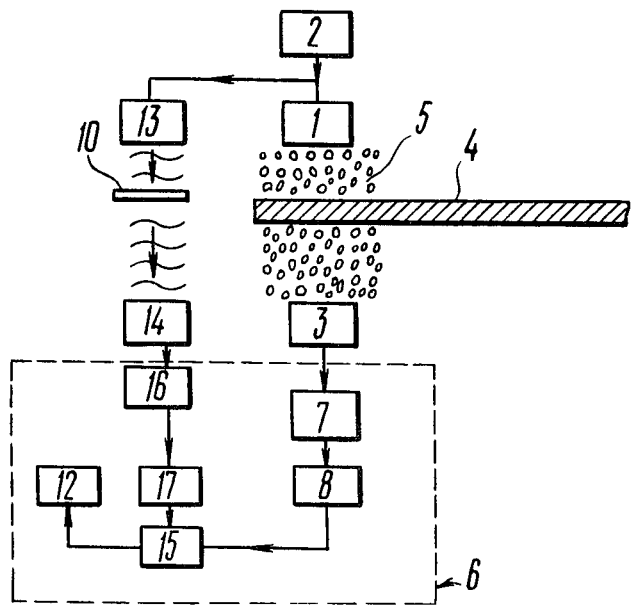
FIG. 2 is a block diagram of another embodiment of the device in accordance with the invention.

Another embodiment of the proposed device is shown in FIG. 2. This embodiment makes it possible to expand the range of measuring thicknesses of sheet materials and reduce the effects of changes in the properties of the acoustically conducting medium 5 and instability of the radiator 1 upon the results of measurements.

Apart from the above-mentioned radiator 1, generator 2, receiver 3, amplifier 7, peak detector 8 and recorder 12, the device shown in FIG. 2 includes an additional acoustical radiator 13 to radiate acoustic oscillation to be sent through the sheet material 10 with a predetermined thickness. The radiator 13 is of a known design similar to that of the main radiator 1. It is connected to the generator 2. The additional radiator 13 makes it possible to reduce errors due to instability of the radiator 1.

In the second embodiment under review, the setter of the reference signal, which is the traveling wave that has passed through the sheet material 10 having a preselected thickness, is an additional receiver 14. The receiver 14 is of a known design similar to that of the receiver 3. The sheet material 10 with a predetermined thickness is placed between the additional radiator 13 and the additional receiver 14, in immediate proximity to the sheet material 4 being checked. As a result, the temperature, pressure and density of the acoustically conducting medium 5, which in this case is air, are very similar or identical in the zone of action of the main radiator 1 and main receiver 3 and in the zone of action of the additional radiator 13 and additional receiver 14. This helps to reduce errors due to changes in the properties of the acoustically conducting medium 5.

The working surfaces of the additional radiator 13 and the additional receiver 14 are roughly parallel to the surface of the sheet material 10 with a predetermined thickness. The distance between the working surfaces of the radiator 13 and receiver 14 is close to the distance between the main radiator 1 and the main receiver 3. As a result, the acoustic oscillation radiated by the additional radiator 13 is sent through the sheet material 10 in the form of a traveling wave.

In the embodiment under review, the unit for comparing the reference signal to a signal carrying information on the thickness of the material 4 being checked is constructed as a division unit 15 of a known design. The additional receiver 14 is electrically connected to one input of the division unit 15 via an additional amplifier 16 and a peak detector 17 which are similar to the main amplifier 7 and the main peak detector 8, respectively. Said additional amplifier 16 and peak detector 17 are serially connected to the additional receiver 14.

Another input of the division unit 15 is connected to an output of the peak detector 8. An output of the division unit 15 is connected to the recorder 12.

The embodiment under review can do without stable properties of the acoustically conducting medium and the sophisticated, high-stability radiator 1. As a result, the acoustically conducting medium can be a gaseous medium which is preferable to a liquid medium. A gaseous medium raises the device's response owing to an accelerated attenuation of acoustic oscillation reflected from the surfaces of the radiators 1 and 13, receivers 3 and 14, and materials 4 and 10. A gaseous medium also rules out instability of the acoustic contact between the radiators 1 and 13 and the receivers 3 and 14 with the material 4 being checked and the material 10 having a preselected thickness, keeping in mind that a loss of contact may occur as a result of a break in the flow of liquid. In addition, the use of a gaseous medium helps to substantially expand the range of measurements, because the density of the sheet material 4 is several times greater than that of the gaseous medium. At the same time, a gaseous medium requires a shorter distance between the radiators 1 and 13 and the receivers 3 and 14, respectively, in order to produce a traveling wave, as the velocity of propagation of acoustic oscillation in a gaseous medium is one order lower than the propagation velocity in a liquid medium. The use of a gaseous medium also rules out corrosion of components of an installation being controlled, for example, a rolling mill.

The device described hereinabove can be successfully employed for measuring absolute thickness values of sheet materials within a broad range throughout the production process without any readjustment of the reference signal setter.

In this embodiment, the unit for comparing the reference signal with the signal carrying information on the thickness of the sheet material being checked may also be constructed as a subtracting unit (not shown) connected to the detectors 8 and 17 and the recorder 12 like the division unit 15. In this case, the device can be employed in systems for automatically controlling production processes, wherein there can be applied to the actuator a control signal proportional to a deviation of the thickness of the sheet material being checked from a specified value.

Figure 3:
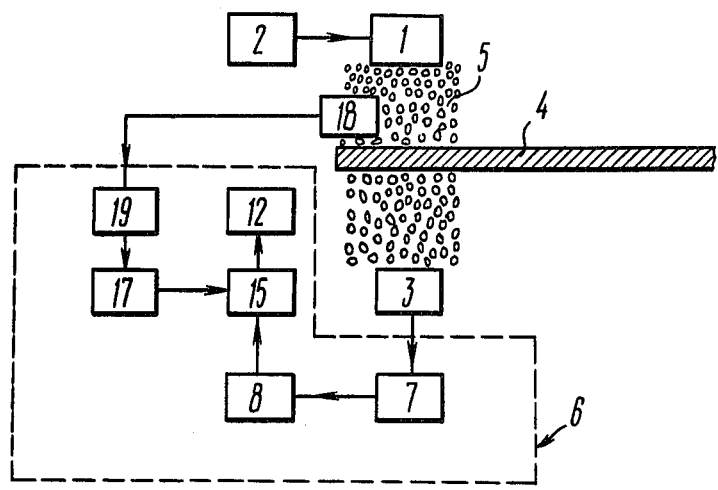
FIG. 3 is a block diagram of still another embodiment of the device in accordance with the invention.

In the embodiment shown in FIG. 3, the setter of the reference signal, whose function is performed by a traveling wave sent through the material 4 being checked, is constructed as an additional receiver 18. The additional receiver 18 is a small-sized piezoelectric microphone (cf. U.S. Pat. No. 3,109,111). The receiver 18 is arranged between the acoustical radiator 1 and the sheet material 4 being checked, across the path of the traveling wave so that a greater part of the traveling wave passes through the material 4 being checked to the main receiver 3, by-passing the additional receiver 18.

The unit for comparing the reference signal to the signal carrying information on the thickness of the sheet material 4 being checked is constructed as the division unit 15. The latter is connected to the peak detector 8 and the recorder 12 and is also electrically coupled to the additional receiver 18. This connection is effected via an amplifier 19 and the peak detector 17 which are serially connected to the receiver 18. The amplifier 19 is provided with a gain factor thermoregulator (not shown) which helps to reduce errors due to changes in the temperature of the air which in the present case is the acoustically conducting medium 5.

The device under review makes it possible to avoid errors in measuring the thickness of the sheet material 4, which are due to instability of the output power of the generator 2 and instability of the acoustical radiator 1. In this case, said instabilities equally affect the acoustic oscillations passing through the sheet material 4 and the acoustic oscillations that have already passed through said material 4 and, therefore, have no effect upon the output voltage of the division unit 15. The result is greater accuracy of measuring the thickness of the sheet material 4.

The foregoing device can be successfully employed for measuring the thickness of sheet materials within a broad range during the entire production process without any readjustment of the reference signal setter.

Figure 4:
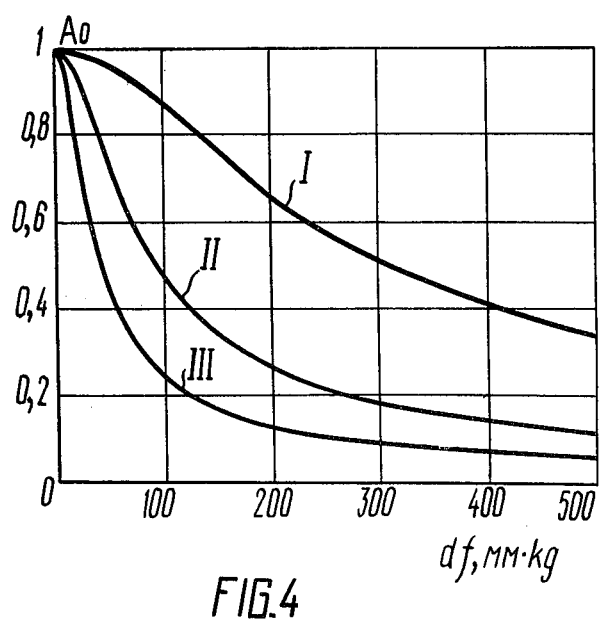
FIG. 4 is a plot showing the dependence of the amplitudes of acoustic oscillation, that has passed and is passing through sheet materials, upon the product of the thickness of the material and the acoustic oscillation frequency.

The proposed method for measuring the thickness of the sheet material 4 being checked is illustrated in FIG. 4 which shows a plot of ratios between the amplitude A of acoustic oscillation being passed through the material and the amplitude $A_o$ of acoustic oscillation that has passed through said material relative to the product of the thickness $d$ of the material 4 (FIG. 1) and the acoustic oscillation frequency $f$. The lines I, II and III (FIG. 4) show these ratios for aluminum, copper and tungsten, respectively.

Analytically, such a dependence can be expressed as follows:

$$\frac{A}{A_o} = \frac{1}{\sqrt{1 + \frac{\rho^2 C^2}{4\rho_o^2 \cdot C_o^2} \cdot \sin^2(\frac{2\pi f d}{C})}} \quad (1),$$

where $\rho_o$ and $C_o$ are the density of the acoustically conducting medium 5 (FIG. 1) and the velocity of propagation of acoustic oscillation in this medium, respectively;

$\rho$ and $C$ are the density of the sheet material 4 being checked and the velocity of propagation of acoustic oscillation in said material 4, respectively.

It is clear from the above expression and plots of FIG. 4 that the amplitude A of the acoustic oscillation that has passed through the sheet material 4 (FIG. 1) is inversely proportional to the latter's thickness $d$.

The proposed method for checking the thickness of sheet materials is effected by the aforementioned devices as follows.

The sheet material 4 (FIG. 1) to be checked is placed between the acoustical radiator 1 and the receiver 3 in water heated to a temperature of 70° to 80° C, which is the acoustically conducting medium.

The generator 2 generates electric pulses which are applied, at a constant repetition period, to the radiator 1. The pulse repetition period is selected depending upon the required thickness measurement accuracy which, in turn, depends upon the number of measurements per unit of time.

The radiator 1 is excited by the electric pulses sent by the generator 2 and sends into the water short, narrow-spectrum acoustic oscillation pulses in the form of a traveling wave. The use of acoustic oscillation in the form of a traveling wave makes it possible to completely eliminate errors in measuring the thickness of the sheet material 4 being checked, which are due to the formation of standing waves which, in turn, are caused by the reflection of the acoustic oscillation from the surfaces of the radiator 1, the receiver 3 and the material 4 being checked, as well as by their superposition upon the acoustic oscillations that have passed through the material 4.

The traveling wave operating conditions are ensured by selecting a distance between the radiator 1 and receiver 3, which is in excess of the spatial extension of the traveling wave during each measurement period.

The acoustic oscillation frequency is selected so that the traveling wave length in the sheet material 4 should be greater than four maximum thicknesses of said material 4 put together. This ensures a single-valued linear dependence between the traveling wave amplitude of the oscillations that have passed through the material 4 and the latter's thickness, whereby the range of measurements in the small-thickness area can be expanded. The above-mentioned ratio between the traveling wave length and the maximum thickness of the sheet material 4 being checked is ensured by using ultrasonic acoustic oscillation for measuring the thickness of film materials (the sheet thickness in this case being less than a few tenths of a millimeter), as well as acoustic oscillation whose frequency lies within the lower portion of the ultrasonic and the upper portion of the audio frequency ranges, the latter frequencies being used for measuring sheet materials of greater thicknesses.

The traveling wave of the acoustic oscillation pulses passes through the sheet material 4 being checked roughly perpendicularly to the latter's surface and enters the water on the opposite side of the material 4 as pulses of a reduced amplitude, as shown in the above expression (1).

The traveling wave passes through the material 4 being checked roughly at a perpendicular to the surface of said material 4, which is due to the fact that the working surfaces of the radiator 1 and receiver 3 are parallel to the surface of the material 4.

The traveling wave pulses that have passed through the sheet material 4 being checked are applied to the receiver 3 which converts them into electric pulses having a carrier frequency equal to the acoustic oscillation frequency. These electric pulses, that carry information on the thickness of the material 4 being checked, are applied to the amplifier 7, which effects amplitude gain, and then proceed to the peak detector 7. The peak detector 7 generates voltage equal to the amplitude of the envelope of pulses applied to its input.

Applied to one input of the subtracting unit 9 from the output of the detector 8 is voltage which is inversely proportional to the thickness of the sheet material 4 being checked. Applied to the other input of the subtracting unit 9 is constant voltage from the output of the d.c. source 11, the latter voltage being inversely proportional to a preselected thickness of the sheet material 10. At the output of the subtracting unit 9 there appears voltage equal to the difference of the voltages applied to its inputs and directly proportional to the difference between the preselected thickness of the sheet material 10 and the thickness of the material 4 being checked.

The output voltage of the subtracting unit 9 is applied to the recorder 12 which indicates the values of deviations of the thickness of the material 4 being checked from the preselected thickness of the sheet material 10.

Prior to the start of operation of the device shown in FIG. 1, the d.c. source 11, which serves as the reference signal setter, is appropriately adjusted. For this purpose, instead of the sheet material 4 to be checked, between the radiator 1 and receiver 3 there is placed the sheet material 10 (FIG. 1) having a predetermined thickness. Through said material 10, there is passed a traveling wave of acoustic oscillation, and the output voltage of the source 11 (FIG. 1) is adjusted to reach a value at which the recorder 12 shows zero.

Normally, the preselected thickness lies at the beginning of the measuring band.

In the course of operation, the output voltage of the source 11 normally remains constant.

The foregoing method of checking the thickness of sheet materials is simple, but makes it possible to carry out measurements within a relatively narrow range of 20 to 40 percent of the predetermined thickness. Further increase in the thickness being measured leads to non-linear dependence of the readings of the recorder 12 upon the thickness of the material, for which reason the d.c. source 11 must be readjusted for a different measuring band.

The range of thicknesses to be measured can also be expanded through the use of the method for checking the thickness of sheet materials effected with the aid of the device of FIG. 2.

According to this method, the sheet material 4 to be checked is placed between the radiator 1 and receiver 3 in the acoustically conducting medium 5 which in the present case is air. Placed between the additional acoustical radiator 13 and the additional receiver 14 is the sheet material 10 of a preselected thickness. Said material 10 is placed in immediate proximity to the material 4 being checked. This reduces errors due to changes in the properties of the acoustically conducting medium which in the present case is air.

The generator 2 generates electric pulses which are applied, at a constant repetition period, to the main radiator 1 and the additional radiator 13.

The radiator 1 sends into the air acoustic oscillation pulses in the form of a traveling wave. These pulses pass through the sheet material 4 being checked, after which their amplitude is reduced according to the above expression (1). Considering that the density $\rho_o$ of air, which is the acoustically conducting medium, is four orders less than the density $\rho$ of the sheet material 4 being checked, we see that $$\frac{\rho^2 C^2}{4\rho_o^2 C_o^2} \cdot \sin^2\left(\frac{2\pi f d}{C}\right) >> 1$$

In addition, in order to avoid excessive weakening of the acoustic oscillation amplitude A, the acoustic oscillation frequency $f$ is selected so that $2\pi f d/C$ should be significantly less than $\pi/2$. The dependence (1) can then be expressed as follows:

$$\frac{A}{A_o} = \frac{\rho_o \cdot C_o}{\pi f \rho \cdot d} \qquad (2)$$

Since $C_o/f = \lambda_o$, where $\lambda_o$ is the length of the traveling wave in the air, the dependence (2) can be expressed as $$\frac{A}{A_o} = \frac{\rho_o \cdot \lambda_o}{\pi \rho d} \text{ or} \qquad (3)$$

$$A = \frac{K}{d} \text{ (4), where } K = \frac{A_o \cdot \rho_o \cdot \lambda_o}{\pi \rho} \qquad (4)$$

It follows from (4) that the amplitude of acoustic oscillations that have passed through the material 4 being checked is in linear and inversely proportional relationship with the thickness of the material 4 being checked, which practically applies to any range of thicknesses.

Acoustic oscillations that have passed through the material 4 being checked are applied to the receiver 3 which converts them into electric pulses. These electric pulses are amplified by the amplifier 7 and applied to the peak detector 8. The latter generates constant voltage equal to the amplitude of the envelope of the electric pulses which arrive at its input. From the output of the detector 8, said voltage is applied to one of the inputs of the division unit 15.

The aforesaid processes are accompanied by the auxiliary radiator 13 radiating into the air acoustic oscillation pulses in the form of a traveling wave. These pulses pass through the sheet material 10 having a predetermined thickness, whereby their amplitude is reduced in accordance with the relationship $$A_1 = K/d_1,$$

where $A_1$ is the amplitude of the acoustic oscillations that have passed through the sheet material 10 with a predetermined thickness.

The receiver 14 receives the weakened pulses and converts them into electric pulses whose carrier frequency is equal to the acoustic oscillation frequency. The amplifier 16 effects amplitude gain of these pulses which are then applied to the peak detector 17. The latter generates constant voltage equal to the amplitude of the envelope of the electric pulses. The output voltage of the detector 17 is applied to the second input of the division unit 15. As a result, at the output of the division unit 15 there appears a voltage equal to the ratio between the voltage applied to its input from the output of the detector 17 and the voltage applied to its second input from the output of the detector 8. Voltage across the output of the division unit 15 is proportional to the thickness of the sheet material 4 being checked. Output voltage of the division unit 15 is applied to the recorder 12 which indicates the thickness of the sheet material 4 being checked.

Prior to the start of operation of the device of FIG. 2, said device is adjusted. For this purpose, instead of the sheet material 4 to be checked, between the radiator 1 and receiver 3 there is placed a sample of said material 4 (not shown) having a known thickness. Through said sample and the sheet material 10, there is sent acoustic oscillation in the form of a traveling wave, and the gain factor of the auxiliary amplifier 16 is adjusted to reach a value at which at the output of the division unit 15 there appears voltage that is directly proportional to the known thickness of said sample; readings of the recorder 12 correspond to said thickness.

This method of checking the thickness of sheet materials ensures high accuracy of thickness measurements within a broad range because the output signal of the division unit 15 is in linear and directly proportional relationship with the thickness of the material being checked. At the same time, the method under review makes it possible to reduce errors due to instability of the transmission factor of the acoustic oscillations as these pass through the material being checked, as well as instability of the output power of the generator 2 and instability of the radiators 1 and 13. This method, however, requires sophisticated equipment for its realization. It can be simplified, though, by using the device of FIG. 3.

In this case, acoustic oscillation is sent through the sheet material 4 to be checked, whereupon it is received by the receiver 3, amplified by the amplifier 7, converted by the detector 8 and applied to the input of the division unit 15 the way it is done in the devices of FIGS. 1 and 2.

Simultaneously, a traveling wave of acoustic oscillation pulses sent into the air by the radiator 1, which in this case serve as the reference signal, is received by the additional receiver 18.

The receiver 18 converts said pulses into electrical pulses whose carrier frequency is equal to the acoustic oscillation frequency. The amplifier 19 effects amplitude gain of the electric pulses. The provision of the amplifier 19 with the gain factor thermoregulator reduces errors due to variations in the air temperature. The amplified electric pulses are applied to the peak detector 17 which generates voltages equal to the amplitude of the envelope of the electric pulses applied to the input of the division unit 15.

As a result, to one of the inputs of the division unit 15 there is applied a voltage which is directly proportional to the amplitude $A_o$ of the traveling wave of the acoustic oscillation being sent through the material 4 being checked; applied to the other input of the division unit 15 is a voltage which is directly proportional to the amplitude A of the traveling wave of the acoustic oscillations that have already passed through the sheet material 4 being checked. At the output of the division unit 15 there appears voltage equal to the ratio between the voltage which is directly proportional to the amplitude $A_o$ of the traveling wave passing through the material 4, and the voltage which is directly proportional to the amplitude A of the traveling wave that has passed through the material 4. According to (2), at the output of the division unit 15 there appears voltage which is directly proportional to the thickness of the material 4 being checked. This voltage is applied to the recorder 12 which indicates the thickness of the material 4 being checked.

Prior to the start of operation of the device of FIG. 3, said device is adjusted like that of FIG. 2.

The proposed method for checking the thickness of sheet materials, effected with the aid of the devices of FIGS. 1, 2 and 3, provides for highly effective contactless automatic checking of the thickness and surface density of sheet materials in production lines in metallurgical, chemical, pulp and paper and other industries.

What is claimed is:

1. A method of checking the thickness of sheet materials by using acoustic oscillations, comprising the steps of placing a sheet of material being checked into an acoustically conducting medium; periodically transmitting acoustic oscillations into the acoustically conducting medium and establishing a travelling wave which is directed in a direction substantially perpendicular to the surface of the sheet; receiving and measuring the transmitted acoustic oscillations in said medium which have passed through the sheet material being checked; comparing the amplitude of the measured acoustic oscillations or signals which have passed through the sheet with a reference signal which has an amplitude corresponding to that of acoustic oscillations or signals passed through material of a predetermined thickness; and determining the thickness of the sheet material being checked based on the relative values of the transmitted and reference signals.

2. A method as defined in claim 1, wherein the acoustic oscillations frequency is selected so that the spatial extension of the travelling wave is greater than four maximum thicknesses of said sheet material.

3. A method as defined in claim 1, further comprising the step of establishing a reference signal in the nature of a travelling wave that has passed through a sheet of material having a predetermined thickness, and whereby comparison of said transmitted and reference signals is achieved by subtracting the amplitude of said transmitted signals from the amplitude of said reference signals.

4. A method as defined in claim 1, further comprising the step of establishing a reference signal in the nature of a travelling wave that has passed through a sheet of material having a predetermined thickness, and whereby comparison of the transmitted and reference signals is achieved by dividing the amplitude of the transmitted signals by the amplitude of the reference signals.

5. A method as defined in claim 1, further comprising the step of establishing a reference signal in the nature of a travelling wave that has passed through said sheet of material being checked, and whereby comparison of the transmitted and reference signals is achieved by dividing the amplitude of the transmitted signals by the amplitude of the reference signals.

6. A method as defined in claim 2, further comprising the step of establishing a reference signal in the nature of a travelling wave that has passed through a sheet of material having a predetermined thickness, and whereby comparison of said transmitted and reference signals is achieved by subtracting the amplitude of the transmitted signals from the amplitude of the reference signals.

7. A method as defined in claim 2, further comprising the step of establishing a reference signal in the nature of a travelling wave that has passed through a sheet of material having a predetermined thickness, and whereby comparison of the transmitted and reference signals is achieved by dividing the amplitude of the transmitted signals by the amplitude of the reference signals.

8. A method as defined in claim 2, further comprising the step of establishing a reference signal in the nature of a travelling wave that has passed through said sheet of material being checked, and whereby comparison of the transmitted and reference signals is achieved by dividing the amplitude of the transmitted signals by the amplitude of the reference signals.

9. A device for checking the thickness of sheet material by using acoustic oscillation, comprising: an acoustical radiator; a generator connected to said acoustical radiator; an acoustical receiver spaced from said radiator; an acoustically conducting medium between the working surfaces of said acoustical radiator and said acoustical receiver which surfaces are roughly parallel to the surface of said sheet material being checked, the sheet material being placed between said radiator and said receiver, the distance between said radiator and said receiver being in excess of the spatial extension of said acoustic oscillation travelling wave in said acoustically conducting medium during each measurement period; an amplifier, an input of said amplifier being connected to an output of said acoustical receiver; a peak detector, an input of said peak detector being connected to an output of said amplifier; a reference signal setter; a comparison unit for comparing a reference signal to a signal carrying information on the thickness of said sheet material being checked, one input of said comparison unit being connected to an output of said peak detector and another input thereof being electrically coupled to said reference signal setter; a recorder connected to an output of said comparison unit for comparing the reference signal to the signal carrying information on the thickness of said sheet material being checked.

10. A device as claimed in claim 9, wherein said reference signal setter comprises an adjustable d.c. source, and said comparison unit comprises a subtracting unit connected to said adjustable d.c. source for comparing the reference signal to the signal carrying information on the thickness of said sheet material being checked.

11. A device as claimed in claim 9, wherein said reference signal setter comprises an additional radiator of acoustic oscillation being passed through a sheet material having a predetermined thickness, an additional receiver of acoustic oscillation, said additional receiver being placed across the path of said acoustic oscillation and providing said reference signal which is in the nature of a travelling wave that has passed through said sheet material having a predetermined thickness; the working surfaces of said additional radiator and receiver being roughly parallel to the surface of said sheet material having a predetermined thickness, which material is placed between said additional radiator and additional receiver which are spaced at a distance in excess of the spatial extension of the travelling wave during each measurement period, said comparison unit comprising a division unit for comparing said reference signal to the signal carrying information on the thickness of said sheet material being checked, said reference signal setter further comprising an additional amplifier whose input is connected to an output of said additional receiver, an additional peak detector whose input is connected to an output of said additional amplifier, whereas its output is connected to an input of said division unit.

12. A device as claimed in claim 9, wherein said reference signal setter comprises an additional acoustical receiver, said additional receiver being placed between said acoustical radiator and said sheet material being checked, across the path of the travelling wave so that part of the travelling wave passes through said sheet material being checked to the first-mentioned acoustical receiver, by-passing said additional receiver, said comparison unit comprising a division unit, said reference signal setter further comprising an additional amplifier whose input is connected to an output of said additional receiver, an additional peak detector whose input is connected to an output of said additional amplifier and its output is connected to an input of said division unit.

* * * * *